United States Patent
Svoboda et al.

[11] Patent Number: 6,158,253
[45] Date of Patent: Dec. 12, 2000

[54] SEAMLESS, FORM FITTING FOOT SOCK

[75] Inventors: Frank Svoboda; H. Darrel Darby, both of Kansas City, Mo.; Jeffrey C. Dalbey, Leawood, Kans.

[73] Assignee: Knit-Rite, Inc., Kansas City, Kans.

[21] Appl. No.: 09/397,421

[22] Filed: Sep. 17, 1999

[51] Int. Cl.[7] .............................. A41B 11/00; D04B 1/26
[52] U.S. Cl. ............................................. 66/178 R; 2/239
[58] Field of Search .................................. 2/239; 66/178 R

[56] References Cited

U.S. PATENT DOCUMENTS

| | | |
|---|---|---|
| 323,287 | 7/1885 | Appleton . |
| 2,004,699 | 6/1935 | Krautkopf . |
| 2,102,369 | 12/1937 | Martel . |
| 2,111,353 | 3/1938 | Berry . |
| 2,318,772 | 5/1943 | Gluck . |
| 2,408,440 | 10/1946 | Norman . |
| 3,006,169 | 10/1961 | Strunk . |
| 3,258,940 | 7/1966 | Shima . |
| 3,338,071 | 8/1967 | Pons et al. . |
| 3,429,147 | 2/1969 | Perrier . |
| 3,451,232 | 6/1969 | Belzidsky . |
| 3,785,173 | 1/1974 | Hanney et al. . |
| 3,916,647 | 11/1975 | Yabuta . |
| 3,975,929 | 8/1976 | Fregeolle . |
| 3,983,870 | 10/1976 | Herbert et al. . |
| 4,109,492 | 8/1978 | Roberts ................................. 66/172 E |
| 4,282,728 | 8/1981 | Tapp et al. ................................. 2/239 |
| 4,571,960 | 2/1986 | Hursh et al. . |
| 4,615,188 | 10/1986 | Hursh et al. . |
| 4,840,635 | 6/1989 | Smith et al. . |
| 5,226,194 | 7/1993 | Staley . |
| 5,412,957 | 5/1995 | Bradberry et al. . |
| 5,487,282 | 1/1996 | Kuhnert . |
| 5,737,943 | 4/1998 | Bernhardt . |

FOREIGN PATENT DOCUMENTS

| | | |
|---|---|---|
| 36907 | 4/1908 | France . |
| 2454766 | 12/1990 | France . |

OTHER PUBLICATIONS

Dubied Knitting Manual, front cover and pp. 1–6 and 57–64 (1967).

"Knitted Stretch Technology", edited by Charles Reichman, published by National Knitted Outerwear Association, front cover, all pages preceding p. 1, pp. 3–11 and 73–108 (1965).

Shima Seiki Instruction Manual No. GBM–101 for Machine Model No. PH015 (Aug., 1992).

*Primary Examiner*—Andy Falik
*Attorney, Agent, or Firm*—Hovey, Williams, Timmons & Collins

[57] ABSTRACT

The highly stretchable, seamless sock conforms to the underlying portion of the body when donned so that there are no undesirable wrinkles or thicknesses in fabric (e.g., ribs, seams, etc) which might cause focal pressure on the foot or leg. The sock comprises a receptacle having an open upper end and an opposite, closed toe end. The receptacle includes a toe section that projects from the toe end and is configured to receive the toes of the wearer, a leg section that is adjacent the leg end and is dimensioned to receive at least a portion of the leg of the wearer, a foot section extending between the leg section and toe section of the receptacle, and a heel section extending partly around the circumference of the receptacle between the foot and leg sections. These sections of the receptacle are knitted of a common high-stretch corespun yarn and are configured to cause the yarn to stretch when the sock is donned. Further, the leg section includes an upper portion that is formed of a distinct knitting pattern, such that the compression exerted by the upper portion is different than that exerted by the other sections of the receptacle. The level of compression exerted by the sock may be varied by changing the knitting pattern used to fabricate the sock or by using a different high-stretch corespun yarn.

38 Claims, 3 Drawing Sheets

SEAMLESS, FORM FITTING FOOT SOCK

BACKGROUND OF THE INVENTION

1. Field of the Invention

The present invention relates generally to foot socks and, more particularly, to a foot sock that is seamless and wrinkle-free when donned so that virtually all the focal pressure points which might otherwise be created by the sock are eliminated.

2. Discussion of Prior Art

In many instances, the configuration of a foot sock can have a profound impact on the wearer's comfort and well being. For example, a wrinkle or thickness (such as a rib or seam) in a sock will likely create focal pressure, friction and skin shear against the underlying portion of the body, particularly when a shoe is worn over the sock. If a person is incapable of sensing any irritation caused at the focal point (e.g., a person suffering from peripheral neuropathy), the problem can go uncorrected and blisters, ulcers or other debilitating conditions can unknowingly be caused. This is particularly problematic with a person having poor circulation, such as some diabetics, because circulatory problems increase the risk of ulceration and the likelihood that such ulcerations can lead to more devastating consequences (e.g., amputation). Furthermore, those ordinarily skilled in the art will appreciate that a person participating in a sporting event, particularly one of long duration (e.g., a marathon), will want to avoid the discomfort normally associated with undesirable wrinkles and thicknesses in a foot sock. It is also possible for an athlete to suffer from the affects of repetitive stress such as friction and skin shear which could result in blisters and reduced performance. Athletes may also benefit from a seamless sock that provides higher compression for better soft tissue support and the reduction of muscle fatigue during sporting activities.

Since the introduction of certain, specialized flatbed knitting machines, it has been possible to knit seamless socks and such socks have been developed in an attempt to eliminate the painful and disabling conditions caused by standard seam-type socks. However, seamless socks have heretofore failed to provide a wrinkle-free fit. Additionally, prior seamless sock designs require centralized areas of compression (e.g., elastic bands or ribs) to maintain the sock in the proper orientation on the body. Furthermore, known seamless sock designs simply do not provide the level of comfort and protection needed by many diabetics, persons with peripheral neuropathy or athletes. Yet another problem with known seamless sock constructions is the fact that they simply utilize standard knitting patterns, which is believed to severely limit the effectiveness of the sock especially in prophylactic applications.

OBJECTS AND SUMMARY OF THE INVENTION

Responsive to these and other problems, an important object of the present invention is to provide a sock that is particularly configured for use by persons suffering from diabetes and/or peripheral neuropathy or athletes such as runners. It is particularly an important object of the present invention to provide a seamless sock that does not include ribs, seams, or other untoward thicknesses. In addition, an important object of the present invention is to provide a sock that eliminates focused pressure and friction points, even when the sock is worn under a shoe. It is also an important object of the present invention to provide a sock that is relatively safer and more comfortable for any user than conventional socks. Another important object of the present invention is to provide a sock that is form fitting and thereby virtually wrinkle-free when worn. A further important object of the present invention is to provide a sock that provides a uniform level of compression without restricting circulation to the foot so as to avoid the highly undesirable so-called "tourniquet effect". In this respect, it is an important object of the present invention to provide a sock that clings to the body without restricting blood flow and while still causing the sock to uniformly conform to the shapes of the body. Still another important object of the present invention is to provide a sock formed by unique knitting patterns that improve the effectiveness and, in some cases, the aesthetics of the sock.

In accordance with these and other objects evident from the following description of the preferred embodiment, the present invention concerns a sock comprising an open top, seamless, fabric receptacle that extends downwardly to a closed toe end. The receptacle includes a tapered toe section that projects from the toe end and is configured to receive the toes of the wearer, a tubular generally straight leg section that is adjacent the leg end and is dimensioned to receive at least a portion of the leg of the wearer, and a tubular generally straight foot section extending between the leg section and toe section. The toe, foot and leg sections of the receptacle are knitted of a common, high-stretch yarn and are configured to cause the yarn to stretch when the sock is donned. Moreover, the yarn comprises multiple corespun strands, each of which includes an elastomeric core and an outer sheath of substantially nonelastic fibers. It is believed that this construction provides a highly stretchable, form fitting sock that is free of seams.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein.

DETAILED DESCRIPTION OF THE PREFERRED EMBODIMENTS

Figure 1:
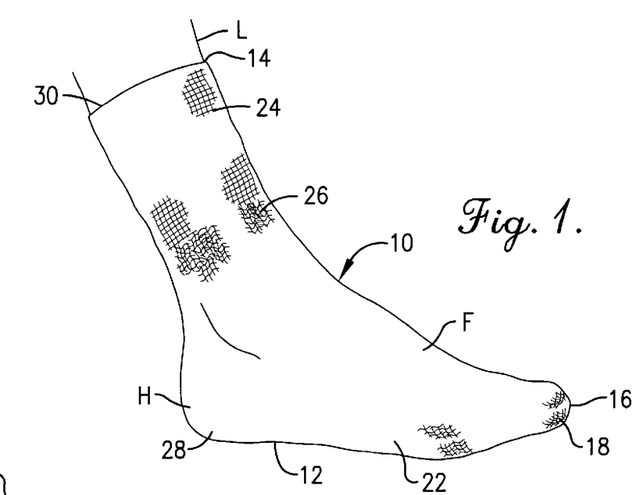
FIG. 1 is a perspective view of a seamless, form fitting foot sock constructed in accordance with the principles of the present invention, particularly illustrating the sock being received on the foot and leg of a wearer.
Figure 2:
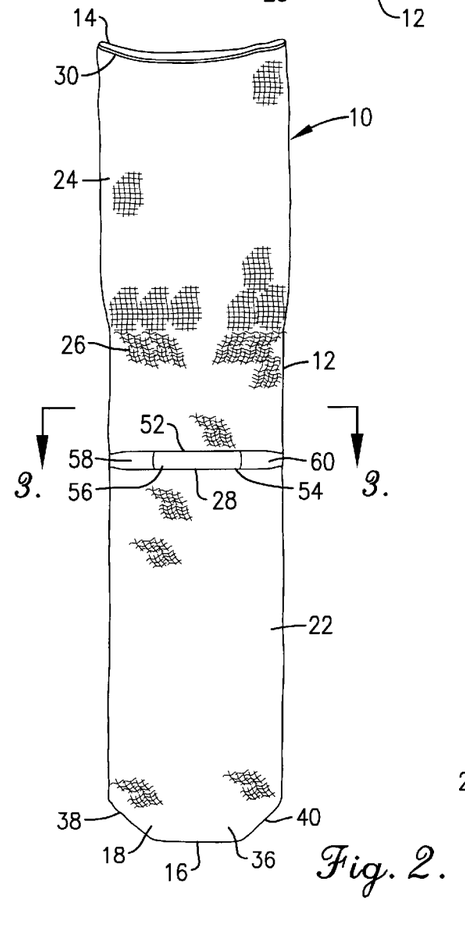
FIG. 2 is an enlarged elevational view of the rear side of the sock shown in FIG. 1.

Turning initially to FIG. 2, the first foot sock 10 selected for illustration comprises an elongated receptacle 12 having an open upper end 14 and an opposite closed toe 16. As shown in FIG. 1, the receptacle 12 is configured to entirely enclose the foot F and extend partly up the leg L beyond the heel H. As will subsequently be described, the receptacle 12 is formed of a fabric knitted of high-stretch yarn, such that the sock 10 presents no seams and is form fitting when donned to eliminate wrinkles.

Figure 5:
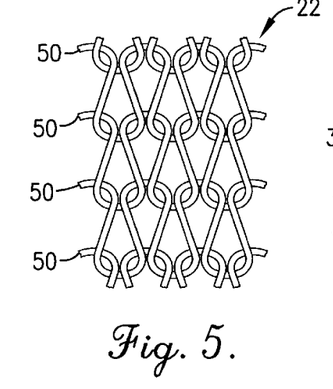
FIG. 5 is a greatly enlarged elevational view of the fabric construction for the toe, foot, heel and lower leg sections of the sock.

The sock 10 is knitted on a specialized flatbed knitting machine (not shown). One such machine is available as Model No. SPH-015 from Shima Seiki Manufacturing, Ltd. of Wakayarna, Japan. It will be appreciated that a standard flatbed knitting machine includes two oppositely inclined flat beds, front and rear, of needles and a yarn carrier or feeder that moves back and forth across the beds to feed yarn to the needles. The needles are shiftable along their respective longitudinal axes to ascend and descend during knitting operations. The machine is particularly well suited for knitting fabric comprising interlacing courses of yarn, with each course typically extending entirely around the knitted article. For example, all of the needles of both beds may be activated so that yarn is fed to and knitted by each of the needles, whereby a tubular, seamless article is formed by courses of plain knit (as described below with respect to FIG. 5). However, certain ones of the needles, including an entire bed, may be deactivated to vary the stitching pattern of the knitted article. In fact, most flatbed knitting machines are programmable to facilitate such activation and deactivation of the needles. It is also noted that the illustrated sock 10 is preferably formed on so-called "ten cut" or "thirteen cut" machines, wherein each bed has ten or thirteen needles per inch, respectively.

The receptacle 12 of the illustrated sock 10 includes seven distinct sections. They include a double stranded closure 18 adjacent the toe end 16 (shown only FIG. 6), a toe section 20 projecting from the toe end 16 (see FIG. 2), a foot section 22 extending from the toe section 20, an upper leg section 24 adjacent the top end 14, a lower leg section 26 extending between the upper leg section 24 and the foot section 22, a heel section 28 located about only part of the circumference of the sock 10 between the lower leg section 26 and the foot section 22, and a top section 30 that defines the upper end 14 and serves to prevent unraveling of the fabric without the need for sewing. The sections 18, 20, 22, 24, 26, 28, 30 cooperatively define the seamless receptacle 12 and are all knitted in seriatim on the knitting machine. It is also noted that the receptacle presents a tubular configuration that is closed at one end and is generally straight (i.e., does not taper) except at the toe and heel sections 20 and 28.

Figure 6:
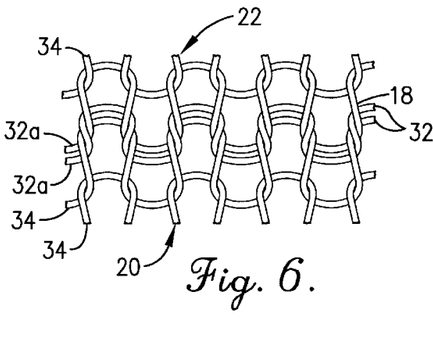
FIG. 6 is a greatly enlarged elevational view of the fabric construction at the closure formed adjacent the toe section when knitting of the sock is first started.

Turning first to the closure 18, the knitting process preferably begins in the usual manner with the carrier of the knitting machine providing yarn alternatively to each of the needles on the front and rear beds. This results in a setup course 32 (see FIG. 6) interlocked with subsequent courses 34 of yarn, as will be described. It will be appreciated that the setup course 32 provides the closure 18 from which the remaining portion of the sock 10 may be formed. That is, once the closure 18 is formed, the subsequent courses 34 may thereafter be knitted to lock in the setup course 32, with the setup course serving to close the sock 10. The setup course 32 may be visually perceptible, but is quite minuscule and adds negligible thickness to the sock. In addition, the setup course 32 is predominately on the outside of the sock 10 so as to provide maximum comfort to the wearer. The setup course 32 (and therefore the closure 18) is preferably provided along the front of the sock 10, which is why it has not been shown in FIG. 2. As will be indicated below, the subsequent courses 34 located below the setup course 32 in FIG. 6 are part of the toe section 20, while the upper subsequent courses 34 are part of the foot section 22. It is also noted that the courses of yarn shown in FIGS. 5–8 will be referenced by different numerals for the sake of clarity; however, certain courses of the sock 10 may very well be represented in more than one of the drawing figures.

Figure 7:
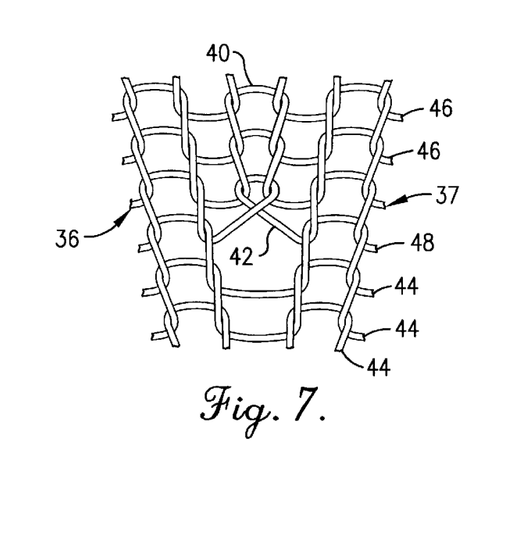
FIG. 7 is a greatly enlarged elevational view of the fabric construction along the tapered lateral extremities of the toe and heel sections of the sock.

The toe section 20 presents a pocket that is configured to receive the toes of the wearer (see FIG. 1). The pocket is defined by a pair of identical panels 36 and 37 (see also FIG. 7) that are collapsible flatly against one another and superimposed when collapsed. It is noted that the toe end 16 has a width that is relatively less than the full width of the sock 10 (e.g., the width of the foot section 22). Thus, the toe section 20 tapers toward the relatively narrow toe end 16. The panels 36,37 present adjacent opposite lateral extremities 38 and 40 that are knitted to one another in such a manner that seams are not formed. Particularly, the toe section 20 is knitted using a full-fashion, knit construction so as to provide the widening from the toe end 16 to the foot section 22 without requiring the panels 36,37 to be sewn to one another. As shown in FIG. 7, a widening fashioning stitch 42 is provided along the extremity 40 between the panels 36 and 37. Those ordinarily skilled in the art will particularly appreciate that each upwardly projecting loop of an illustrated course corresponds with one needle. In this respect, the portions of the three lower courses 44 shown in FIG. 7 are knit by only two needles, while the portions of the upper courses 46 shown in FIG. 7 are knit by three needles. The fashioning course 48 involves the addition of a needle such that the upper courses 46 are wider than the lower courses 44. Although not shown, it will be appreciated that a similar fashioning stitch is provided in the course 48 along the opposite extremity 38. The fashioning stitches 42 present very slight irregularities along the extremities 38 and 40, with the irregularities presenting a slightly discernable line that is predominately on the outside of the sock 10.

The toe section 20 is preferably formed by only one of the beds of the knitting machine. The needles of the other bed are consequently deactivated but still hold onto the setup course 32. The needles at the opposite ends of the activated bed are gradually deactivated (e.g., after every course), with each deactivated needle descending to no longer accept yarn from the carrier but still holding onto whatever yarn has been fed thereto before it descends. This causes the courses to narrow. Once the remaining activated needles present a width corresponding to the relatively narrow toe end 16, the deactivated needles will be gradually reactivated in a reverse manner to widen the courses. Such reactivation creates the fashioning stitch 42 shown in FIG. 7. In view of the foregoing, the front panel 37 is knitted while the needles are gradually deactivated, while the rear panel 36 is formed as the needles gradually reactivate.

Once all of the needles have been reactivated, the knitting bed will have the same needles activated as those used to create the setup course 32. At this point, both beds of the knitting machine are activated and formation of the foot section 22 is commenced. It may therefore be said that the illustrated foot section 22 begins at the first full width course (i.e., at the course just above the tapering toe section 20). It is particularly noted that the foot section 22 presents a straight, tubular shape that does not taper, and knitting of this section consequently involves activation of the same number of needles on both beds as the full length of the section 22 is knitted. Moreover, the foot section 22 is preferably formed of a standard so-called "plain knitting pattern". As particularly shown in FIG. 5, such a knitting pattern comprises identical interlacing looped courses 50. Furthermore, the stitching pattern is continuous along the entire length of the course, such that the stitch cooperatively formed between the beds is the same as the stitches formed in each of the beds. The foot section 22 consequently has no discernable side or edge. It will be appreciated that the generally aligned vertical portions of the interlaced loops present wales that extend along the length of the sock 10, while the interlaced portions of the loops present transverse rounds (see FIG. 5). Preferably, the receptacle 12 is knitted so that the wales are more discernable on the outside of the sock 10 and the rounds are more discernable on the inside. It is also noted that the toe section 20 is similarly formed of plain knit courses (see FIGS. 6 and 7), at least some of which include fashioning stitches at the opposite extremities 38 and 40 to narrow or widen the knitted panel.

Figure 3:
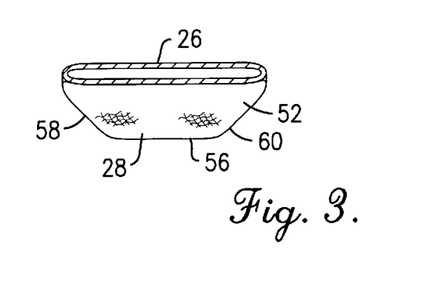
FIG. 3 is cross-sectional view of the sock taken along line 3—3 of FIG. 2, particularly illustrating the heel section of the sock.

As perhaps best shown in FIGS. 2 and 3, the heel section 28 is similar in construction to the toe section 20. Particularly, the heel section 28 comprises a pocket defined by a pair of identical sidewalls 52 and 54. The sidewalls 52 and 54 are collapsible flatly against one another and are superimposed when collapsed (see particularly FIG. 2). The heel pocket 28 presents an outermost end 56 having generally the same width as the toe end 16, and the sidewalls 52 and 54 cooperatively present lateral extremities 58 and 60 that taper as the end 56 is approached. The heel pocket 28 is preferably formed of plain knit courses, some of which include fashioning stitches (similar to that shown in FIG. 7) at the opposite extremities 58 and 60. Knitting of the heel pocket 28 will consequently be accomplished in virtually the same manner as knitting of the toe section 20, with the same beds being respectively activated and deactivated. Because the heel section 28 is knitted by only one bed, it projects from only the rear side of the sock 10. That is, the heel section 28 extends only partly around the circumference of the sock 10.

Once knitting of the heel section 28 is completed, the deactivated bed is reactivated and both beds are used to form the lower leg section 26. Preferably, the lower leg section 26 is knitted in the same manner as the foot section 22, whereby the lower leg section 26 has a straight tubular configuration presenting no discernable sides or edges (e.g., see FIG. 3).

Figure 8:
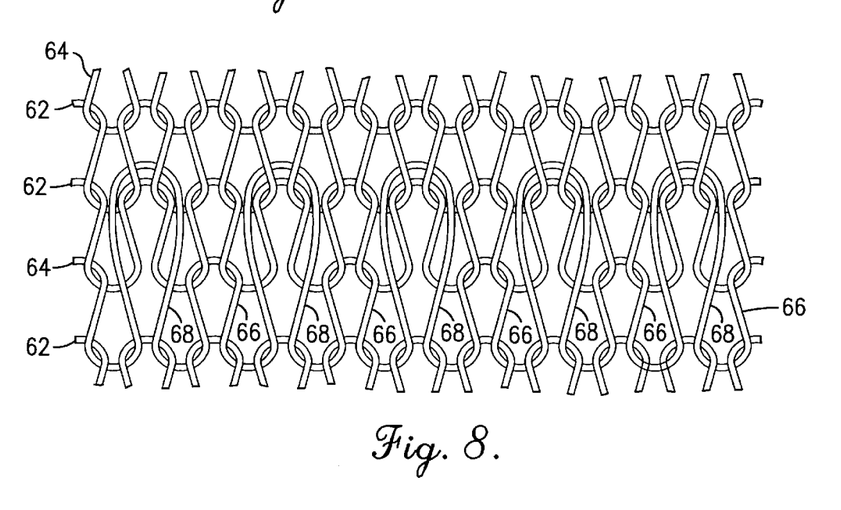
FIG. 8 is a greatly enlarged elevational view of the fabric construction for the upper leg section and top section of the sock.

On the other hand, the illustrated upper leg section 24 is provided with a distinct knitting pattern that differs from that of the toe, foot, heel and lower leg sections. This difference in knitting patterns is represented in FIGS. 1 and 2 by two distinct types of shade patterning, and this difference on an actual sock is also likely to be visually perceptible. However, it will be appreciated that the upper leg section 24 has a straight tubular configuration similar to the lower leg section 26 and foot section 22. Furthermore, the knitting of the upper leg section 24 preferably involves the use of the same number of needles on each of the activated beds as those used in the lower leg and foot sections 22 and 24. In the embodiment shown in FIGS. 1-8, the distinct knitting pattern comprises a plurality of interlacing looped knit-and-tuck courses (as shown in FIG. 8). Specifically, the knitting pattern includes two plain knit courses 62 between every two tuck courses 64. The preferred tuck course 64 comprises alternating plain and tuck stitches 66 and 68, respectively. In this respect, every other needle on the beds knits a tuck stitch when the tuck course 64 is formed. It is also noted that each tuck stitch 68 interlaces with the second subsequently formed plain knit course (i.e., the uppermost plain knit course shown in FIG. 8). This will be accomplished by having the corresponding needle fully ascend to accept the yarn of the tuck course 64 followed by only half ascension of the needle so that the tuck course is not cast off but the next plain knit course is received by the needle. Both pieces of yarn are held within the hook of the needle and the needle is subsequently fully ascended to first receive the yarn of the second plain knit course and then interlace and cast off all three courses. Those ordinarily skilled in the art will appreciate that the knitting pattern shown in FIG. 8 is relatively looser, and therefore more stretchable, than the plain knit pattern shown in FIG. 5. As will be described further below, the toe, foot, heel and upper and lower leg sections are formed of the same type of high-stretch yarn and therefore the upper leg section 24 will likely exert less constriction against the body than the other sections of the receptacle (assuming of course the sections are stretched to generally the same degree).

The top section 30 of the receptacle 12 is preferably knit in the same manner as the upper leg section 24. However, the top section is preferably formed of yarn that is capable of fusing the stitching at the upper end 14 of the receptacle 12 so that unraveling of the fabric may be avoided without requiring traditional sewing techniques (i.e., without requiring a seam). In the preferred embodiment, the top section 30 is knitted from a heat fusing yarn such as that available under the designation "PORTE" from Nitto Boseki Co., Ltd. of Japan. The sock 10 is preferably washed in hot water before it is packaged to cause the PORTE brand yarn to fuse and seal the top of the sock 10. Again, this will prevent fraying and unraveling of the unsewn upper end 14 of the receptacle 12.

Figure 4:
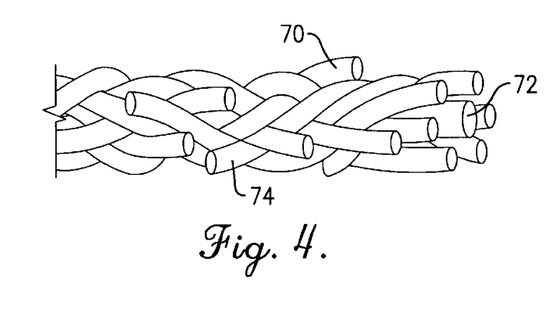
FIG. 4 is a fragmentary elevational view of the corespun yarn used to knit the sock.

With respect to the other sections of the receptacle 12, it is critical that a corespun high-stretch yarn be used. It is believed that this unique application of a corespun yarn unexpectedly and greatly enhances the hand and form fitting nature of the sock 10, without causing the sock 10 to unduly constrict the underlying portions of 30 the body. A standard, high-stretch corespun strand is referenced by the numeral 70 in FIG. 4 and includes an elastomeric core 72 inside a nonelastic fiber sheathing 74. Those ordinarily skilled in the art will appreciate that high-stretch corespun strands are formed by a special technique and the strand 70 is consequently twisted and thereby has a torsional bias about its longitudinal axis. The present invention involves combining multiple corespun strands to form the yarn used in knitting the toe, foot, heel, and upper and lower leg sections 20–28, such that the torsional biases of the strands are canceled. This may be accomplished a number of ways. In the preferred embodiment, two oppositely twisted strands (referred to as "Z-twist" and "S-twist" strands) are combined so that their oppositely directed torsional biases cancel one another out. Typically, the oppositely twisted strands are simultaneously routed to the knitting machine carrier from respective sources and the strands simply cling to one another (i.e., they are not otherwise positively attached or adhered to one another before knitting). Alternatively, it is possible to use a plied corespun yarn, wherein two or more similarly twisted strands (e.g., two Z-twist strands) are twisted about one another in an opposite direction (e.g., in the "S" direction when the two Z-twist strands are combined).

In the preferred embodiment, the core 72 of each strand 70 is formed of a twenty denier spandex filament. Such a material may be purchased under the designation "LYCRA" from E. I. DuPont Nemours & Co., Inc. of Wilmington, Del. The preferred sheathing 74 comprises slivers of blended fibers that serve to wick moisture away from the body, improve the breathability of the sock, and inhibit fungus and bacteria growth. It has particularly been determined that a suitable sheathing blend includes channeled polyester fiber and an antimicrobial acetate fiber. The channels of the polyester fiber serve to pull heat generated moisture from the body to the outer layer of the fabric which has an increased surface area relative to the skin, thereby enhancing evaporation. One suitable channeled polyester fiber is also available from DuPont under the designation "COOLMAX". The antimicrobial fiber serves to control bacteria-related odors and stains and create more hygienic and comfortable conditions. A suitable antimicrobial acetate fiber is available under the designation "MICROSAFE" from Celanese Acetate of Rockhill, S.C. Again, the preferred corespun yarn is comprised of channeled polyester fiber, antimicrobial fiber and spandex. The amount of spandex may be increased or decreased according to the level of compression and support desired. However, one suitable yarn composition comprises approximately 2.3% spandex, approximately 82.7% channeled polyester fiber, and approximately 15% antimicrobial fiber.

The use of the corespun yarn causes the sock 10 to be highly stretchable. For example, with the preferred twenty denier corespun strand 70, the plain knit portions of the sock 10 (i.e., the toe section 20, the foot section 22, the heel section 28 and the lower leg section 26) are elastically stretchable approximately 210% in the longitudinal direction of the sock 10 (i.e., along the length of the foot or leg) and approximately 205% in a transverse direction (i.e., about the foot or leg). This stretchability causes the sock to conform to the contours of the underlying portions of the body, without restricting circulation. Furthermore, the risk of wrinkles is greatly reduced when the sock 10 is donned. In addition, the receptacle 12 is configured so that the toe, foot, heel and lower leg sections are stretched when the sock 10 is donned. Accordingly, the risk of wrinkles is virtually eliminated and there is essentially no need to provide the sock 10 with elastic bands or ribs to prevent downward migration of the sock 10.

Because of the relatively loose nature of the knitting pattern used in the upper leg section 24, this section of the receptacle is elastically stretchable up to approximately 275% of its original, unstretched size. The upper leg section 24 consequently provides the form fitting qualities of the plain knit sections but also ensures that undue compression is not exerted adjacent the top of the sock. It has been determined that such undue compression is likely to create a tourniquet effect and thereby constrict blood flow to the foot. It is noted that the heat melting yarn is somewhat frangible (without losing its fusing properties) and therefore provides little, if any, restriction to the stretchability of the upper leg section 24. It may be said that the sock 10 is particularly suitable for use by a person afflicted with diabetes and/or peripheral neuropathy.

Figure 9:
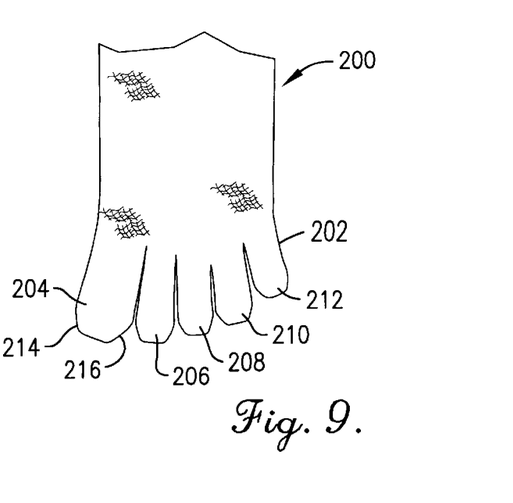
FIG. 9 is an elevational view of a second embodiment of the present invention, wherein the toe section includes a separate toe pocket for each of the toes of the foot.

A second embodiment of the present invention is shown in FIG. 9, wherein the illustrated sock 200 is similar in construction to the sock 10 shown in FIGS. 1–3, except for a unique toe section 202 comprising individual toe pockets 204, 206, 208, 210, 212. It is particularly noted that the toe pockets 204, 206, 208, 210, 212 are knitted one at a time and are separate until laterjoined. Furthermore, a setup course (not shown) is defined at the end of each of the toe pockets 204, 206, 208, 210, 212 and both needle beds are consequently used to knit each pocket. As shown in FIG. 9, the pocket 204 for the big toe includes two downwardly tapering extremities 214 and 216, but is otherwise straight and tubular. Accordingly, the toe pocket 204 is preferably formed of plain knit courses, with the lowermost courses having suitable fashioning stitches (similar to that shown in FIG. 7) at the lateral extremities 214 and 216. It will be appreciated that the other toe pockets (i.e, the second to fifth toe pockets 206, 208, 210, 212) are similarly constructed. Once a toe pocket is formed, the needles used to knit that pocket are deactivated but do not release the pocket. The needles are then reactivated when the pocket is to be joined by standard interweaving stitches with adjacent pocket(s).

The toe sock 200 is also highly suitable for use by diabetics or anyone suffering from fungal infections on the foot. Particularly, the form fitting toe pockets 204, 206, 208, 210, 212 permit air to circulate between the toes so as to enhance the wicking action of the preferred corespun yarn. Furthermore, the fabric provided between the toes prevents direct toe contact and consequently reduces friction between the toes. The toe sock 200 may consequently be used as a prophylaxis or treatment for toe injuries (e.g., blisters, ulcers, etc.).

Figure 10:
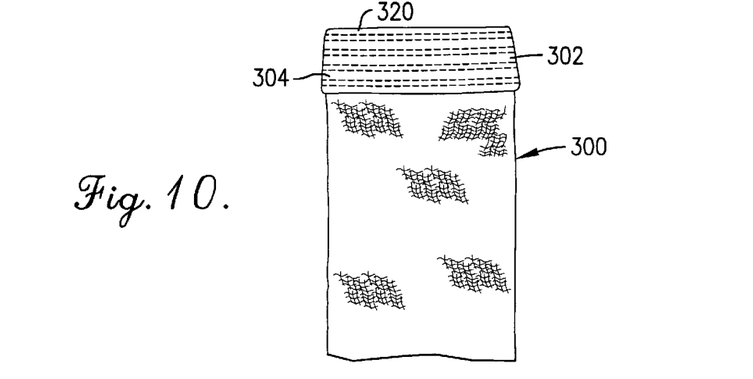
FIG. 10 is an elevational view of a third embodiment of the present invention, wherein the upper leg section of the sock includes a folded cuff and is provided with elastic yarn.
Figure 11:
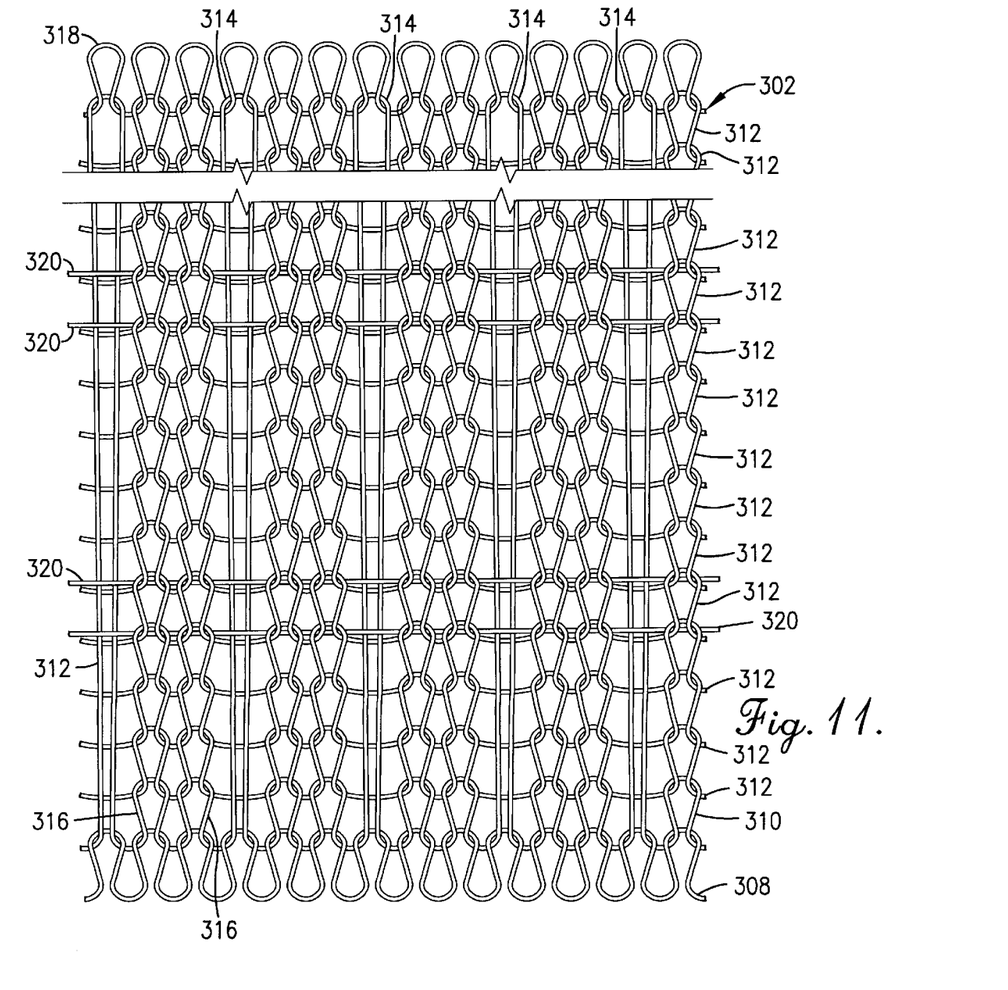
FIG. 11 is a greatly enlarged view of the fabric construction for the top section of the sock shown in FIG. 10.

A third embodiment of the present invention is disclosed in FIGS. 10–11 as comprising a sock 300 upper leg section 302 formed into a folded over cuff 304 as a result of the distinct interlacing looped knitting pattern shown in FIG. 11. Particularly, the upper leg section 302 begins with a first plain knit course 306, although this course may alternatively comprise the last course of the lower leg section 308 if desired. A cuff-forming course 310 is then formed, followed by a plurality of intermediate plain knit courses 312. It is specifically noted that several of the needles are deactivated once the yarn of the cuff-forming course 310 has been fed thereto (note, the yarn is not cast off by the deactivated needles but is instead held so that it may be later interlaced with another course). Each of the deactivated needles forms a connecting loop 314. In the preferred embodiment, the cuff-forming course includes a connecting loop 314 between every two plain knit loops 316. The upper leg section 302 also includes a final plain knit course 318 and it is at this point that the deactivated needles are reactivated so that the connecting loops 314 interlace with the final course 318. This causes the upper leg section 302 to fold over and be connected to itself.

Furthermore, elastic strands 320 are preferably laid into the upper leg section 302 as it is being knitted. Laying in of the strands 320 does not involve stitching with the courses, but rather the strands 320 are simply laid in between the stitches of the loops in the overall fabric. Preferably, the strands 320 are arranged in pairs, with each strand of a pair being laid along a respective one of two adjacent, interlacing intermediate courses 312. The pairs of strands 320 are preferably separated by four intermediate courses 312. The elastic strands may be formed of any suitable material (e.g., high stretch nylon or polyester filament, a corespun yarn, or a covered spandex). The preferred elastic strand material comprises a latex-free covered yarn consisting of a spandex core and a stretch nylon covering. Such a material is available as Style No. 235 from Supreme Corporation of Hickory, N.C.

Preferably, the sock 300 is knitted of forty denier spandex corespun strands. In this respect, the sock 300 is not as stretchable as the sock 10 and the former is consequently configured to provide greater overall compression and soft tissue support to the underlying portions of the body. It has been determined that this arrangement improves microcirculation within the underlying portions of the body. The sock 300 is consequently believed to reduce muscle fatigue and to be particularly suitable for use in sports applications.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A highly stretchable, seamless foot sock that conforms to the underlying portions of the body when donned, said sock comprising:

a seamless, elongated fabric receptacle for receiving the foot and at least a portion of the leg, of the wearer, said receptacle presenting an open leg end, through which the foot and leg of the wearer are inserted when the sock is donned, and a closed toe end, said receptacle including a toe section that is at least in part tapered toward the toe end and projects from the toe end for receiving the toes of the wearer, a tubular generally straight leg section that is adjacent the leg end and is dimensioned to receive at least a portion of the leg of the wearer, and a tubular generally straight foot section extending between the leg section and toe section of the receptacle, said toe, foot and leg sections of the receptacle being knitted of a common high-stretch yarn and being generally undersized in an unstretched condition relative to the underlying portions of the body, such that the yarn of the toe, foot and leg sections is resiliently stretched when the sock is donned, said yarn comprising a corespun yarn that includes an elastomeric core and an outer sheath comprising substantially nonelastic fibers.

2. A foot sock as claimed in claim 1,
said elastomeric core comprising a spandex filament.

3. A foot sock as claimed in claim 1,
said leg section including an upper portion adjacent the top end of the receptacle and a lower portion that extends between the upper portion and the foot section,
said upper portion of the leg section being formed of a distinct knitting pattern that is different from that of the lower portion of the leg section.

4. A foot sock as claimed in claim 3,
said distinct knitting pattern comprising a plurality of interlacing looped knitand-tuck courses.

5. A foot sock as claimed in claim 3,
said distinct knitting pattern comprising a plurality of interlacing looped cuff-forming courses that cause said upper portion of the leg section to form a folded over cuff.

6. A foot sock as claimed in claim 5,
said cuff-forming courses including a final course that defines one circumferential extremity of the upper portion of the leg section, a connecting course, and a plurality of intermediate courses located between the connecting course and final course,
said connecting course including a plurality of spaced apart connecting loops that extend across the intermediate courses and interlace with the final course.

7. A foot sock as claimed in claim 6,
said connecting course including a pair of plain knit loops between every two of the connecting loops.

8. A foot sock as claimed in claim 7,
said distinct knitting pattern including a plurality of circumferential, auxiliary elastic strands laid in the cuff-forming courses.

9. A foot sock as claimed in claim 8,
said elastic strands being arranged in pairs, with each of the pairs of elastic strands being laid in a respective interlacing pair of the intermediate courses,
said pairs of elastic strands being spaced apart by four of the intermediate courses.

10. A foot sock as claimed in claim 3,
said toe section comprising at least one toe pocket dimensioned to receive at least one of the toes of the wearer therein,
said at least one toe pocket including two knitted panels that are collapsible flatly against one another,
said panels presenting opposite lateral extremities that taper toward the toe end, with the panels being at least partly interconnected along each of the extremities by fashion stitches.

11. A foot sock as claimed in claim 10,
said receptacle including a heel section configured to receive the heel of the wearer therein,
said heel section being knitted of the common high-stretch yarn and extending only partly around the circumference of the receptacle between the foot section and the lower portion of the leg section,
said heel section comprising a heel pocket that presents a closed end and includes two knitted sidewalls which are collapsible flatly against one another,
said sidewalls tapering toward the closed end and being at least partly interconnected along their opposite lateral extremities by fashion stitches.

12. A foot sock as claimed in claim 11,
said toe, foot and heel sections and the lower portion of the leg section all being formed of plain knit courses.

13. A foot sock as claimed in claim 11,
said receptacle including a top section projecting from the top end thereof,
said top section being knitted of a heat fusible yarn that prevents fraying of the receptacle when melted.

14. A foot sock as claimed in claim 1,
said sheath including moisture transporting fibers.

15. A foot sock as claimed in claim 1,
said sheath including antimicrobial fibers.

16. A foot sock as claimed in claim 1.
said yarn comprising multiple corespun strands, each of which includes an elastomeric core and an outer sheath comprising substantially nonelastic fibers.

17. A foot sock as claimed in claim 1,
said toe section comprising a plurality of toe pockets, each being dimensioned to receive one of the toes of the wearer therein, each of said toe pockets including two knitted panels that are collapsible flatly against one another, with the panels presenting opposite lateral extremities that taper toward the toe end, said panels being at least partly interconnected along each of the extremities by fashion stitches.

18. A highly stretchable, seamless foot sock that conforms to the underlying portions of the body when donned, said sock comprising:

a seamless, elongated fabric receptacle for receiving the foot and at least a portion of the leg of the wearer, said receptacle presenting an open leg end, through which the foot and leg of the wearer are inserted when the sock is donned, and a closed toe end, said receptacle including a toe section that is at least in part tapered toward the toe end and projects from the toe end for receiving the toes of the wearer, a tubular generally straight leg section that is adjacent the leg end and is dimensioned to receive at least a portion of the leg of the wearer, and a tubular generally straight foot section extending between the leg section and toe section of the receptacle, said toe, foot and leg sections of the receptacle being knitted of a common high-stretch yarn and being configured to cause the yarn to stretch when the sock is donned, said yarn comprising multiple corespun strands, each of which includes an elastomeric core and an outer sheath of substantially nonelastic fibers, said elastomeric core comprising a spandex filament, said sheath including channeled polyester fibers.

19. A foot sock as claimed in claim 18, said sheath including antimicrobial acetate fibers.

20. A foot sock as claimed in claim 19, said leg section having at least a portion thereof that is formed of a distinct knitting pattern that is different from that of the toe and foot sections and any remaining portion of the leg section.

21. A foot sock as claimed in claim 20, said distinct knitting pattern comprising a plurality of interlacing looped knit-and-tuck courses.

22. A foot sock as claimed in claim 21, said knit-and-tuck courses including a plurality of tuck courses, each having every other loop formed of a tuck stitch, and a plurality of plain knit courses, with there being two plain knit courses between every two tuck courses.

23. A foot sock as claimed in claim 20, said distinct knitting pattern comprising a plurality of interlacing looped cuffforming courses that cause said at least a portion of the leg section to form a folded over cuff.

24. A foot sock as claimed in claim 23, said cuff-forming courses including a final course that defines one circumferential extremity of said at least a portion of the leg section, a connecting course, and a plurality of intermediate courses located between the connecting course and final course, said connecting course including a plurality of spaced apart connecting loops that extend across the intermediate courses and interlace with the final course.

25. A foot sock as claimed in claim 24, said connecting course including a pair of plain knit loops between every two of the connecting loops.

26. A foot sock as claimed in claim 24, said distinct knitting pattern including a plurality of circumferential, auxiliary elastic strands laid in the cuff-forming courses.

27. A foot sock as claimed in claim 26, said elastic strands being arranged in pairs, with each of the pairs of elastic strands being laid in a respective interlacing pair of the intermediate courses, said pairs of elastic strands being spaced apart by four of the intermediate courses.

28. A highly stretchable, seamless foot sock that conforms to the underlying portions of the body when donned, said sock comprising:

a seamless, elongated fabric receptacle for receiving the foot and at least a portion of the leg of the wearer, said receptacle presenting an open leg end, through which the foot and leg of the wearer are inserted when the sock is donned, and a closed toe end, said receptacle including a toe section that is at least in part tapered toward the toe end and projects from the toe end for receiving the toes of the wearer, a tubular generally straight leg section that is adjacent the leg end and is dimensioned to receive at least a portion of the leg of the wearer, and a tubular generally straight foot section extending between the leg section and toe section of the receptacle, said toe, foot and leg sections of the receptacle being knitted of a common high-stretch yarn and being configured to cause the yarn to stretch when the sock is donned, said yarn comprising multiple corespun strands, each of which includes an elastomeric core and an outer sheath of substantially nonelastic fibers, said leg section including an upperportion adjacent the top end of the receptacle and a lower portion that extends between the upper portion and the foot section, said upper portion of the leg section being formed of a distinct knitting pattern that is different from that of the lower portion of the leg section, said distinct knitting pattern comprising a plurality of interlacing looped knit-and-tuck courses, said knit-and-tuck courses including a plurality of tuck courses, each having every other loop formed of a tuck stitch, and a plurality of plain knit courses, with there being two plain knit courses between every two tuck courses.

29. A highly stretchable, seamless foot sock that conforms to the underlying portions of the body when donned, said sock comprising;

a seamless, elongated fabric receptacle for receiving the foot and at least a portion of the leg of the wearer, said receptacle presenting an open leg end, through which the foot and leg of the wearer are inserted when the sock is donned, and a closed toe end, said receptacle including a toe section that is at least in part tapered toward the toe end and projects from the toe end for receiving the toes of the wearer, a tubular eternally straight leg section that is adjacent the leg end and is dimensioned to receive at least a portion of the leg of the wearer, and a tubular generally straight foot section extending between the leg section and toe section of the receptacle, said toe, foot and leg sections of the receptacle being knitted of a common high-stretch yarn and being configured to cause the yarn to stretch when the sock is donned, said yarn comprising multiple corespun strands, each of which includes an elastomeric core and an outer sheath of substantially nonelastic fibers, said leg section including an upper portion adjacent the top end of the receptacle and a lower portion that extends between the upper portion and the foot section, said upper portion of the leg section being formed of a distinct knitting pattern that is different from that of the lower portion of the leg section, said distinct knitting pattern comprising a plurality of interlacing looped cuff-forming courses that cause said upper portion of the leg section to form a folded over cuff, said cuff-forming courses including a final course that defines one circumferential extremity of the upper portion of the leg section, a connecting course, and a plurality of intermediate courses located between the connecting course and final course, said connecting course including a plurality of spaced apart connecting loops that extend across the intermediate courses and interlace with the final course.

30. A foot sock as claimed in claim 29, said connecting course including a pair of plain knit loops between every two of the connecting loops.

31. A foot sock as claimed in claim 30, said distinct knitting pattern including a plurality of circumferential, auxiliary elastic strands laid in the cuff-forming courses.

32. A foot sock as claimed in claim 31, said elastic strands being arranged in pairs, with each of the pairs of elastic strands being laid in a respective interlacing pair of the intermediate courses, said pairs of elastic strands being spaced apart by four of the intermediate courses.

33. A highly stretchable, seamless foot sock that conforms to the underlying portions of the body when donned, said sock comprising:

a seamless, elongated fabric receptacle for receiving the foot and at least a portion of the leg of the wearer, said receptacle presenting an open leg end, through which the foot and leg of the wearer are inserted when the sock is donned, and a closed toe end, said receptacle including a toe section that is at least in part tapered toward the toe end and projects from the toe end for receiving the toes of the wearer, a tubular generally straight leg section that is adjacent the leg end and is dimensioned to receive at least a portion of the leg of the wearer, and a tubular generally straight foot section extending between the leg section and toe section of the receptacle, said toe, foot and leg sections of the receptacle being knitted of a common high-stretch yarn and being configured to cause the yarn to stretch when the sock is donned, said yarn comprising multiple corespun strands, each of which includes an elastomeric core and an outer sheath of substantially nonelastic fibers, said leg section including an upper portion adjacent the top end of the receptacle and a lower portion that extends between the upper portion and the foot section, said upper portion of the leg section being formed of a distinct knitting pattern that is different from that of the lower portion of the leg section, said toe section comprising at least one toe pocket dimensioned to receive at least one of the toes of the wearer therein, said at least one toe pocket including two knitted panels that are collapsible flatly against one another, said panels presenting opposite lateral extremities that taper toward the toe end, with the panels being at least partly interconnected along each of the extremities by fashion stitches.

34. A foot sock as claimed in claim 33, said receptacle including a heel section configured to receive the heel of the wearer therein, said heel section being knitted of the common high-stretch yarn and extending only partly around the circumference of the receptacle between the foot section and the lower portion of the leg section, said heel section comprising a heel pocket that presents a closed end and includes two knitted sidewalls which are collapsible flatly against one another, said sidewalls tapering toward the closed end and being at least partly interconnected along their opposite lateral extremities by fashion stitches.

35. A foot sock as claimed in claim 34, said toe, foot and heel sections and the lower portion of the leg section all being formed of plain knit courses.

36. A foot sock as claimed in claim 34, said receptacle including a top section projecting from the top end thereof, said top section being knitted of a heat fusible yarn that prevents fraying of the receptacle when melted.

37. A highly stretchable, seamless foot sock that conforms to the underlying portions of the body when donned, said sock comprising:

a seamless, elongated fabric receptacle for receiving the foot and at least a portion of the leg of the wearer, said receptacle presenting an open leg end, through which the foot and leg of the wearer are inserted when the sock is donned, and a closed toe end, said receptacle including a toe section that is at least in part tapered toward the toe end and projects from the toe end for receiving the toes of the wearer, a tubular generally straight leg section that is adjacent the leg end and is dimensioned to receive at least a portion of the leg of the wearer, and a tubular generally straight foot section extending between the leg section and toe section of the receptacle, said toe, foot and leg sections of the receptacle being knitted of a common high-stretch yarn and being configured to cause the yarn to stretch when the sock is donned, said yarn comprising multiple corespun strands, each of which includes an elastomeric core and an outer sheath of substantially nonelastic fibers, said toe section comprising a plurality of toe pockets, each being dimensioned to receive one of the toes of the wearer therein, each of said toe pockets including two knitted panels that are collapsible flatly against one another, with the panels presenting opposite lateral extremities that taper toward the toe end, said panels being at least partly interconnected along each of the extremities by fashion stitches.

38. A highly stretchable, seamless foot sock that conforms to the underlying portions of the body when donned, said sock comprising:

a seamless elongated fabric receptacle for receiving the foot and at least a portion of the leg of the wearer, said receptacle presenting an open leg end, through which the foot and leg of the wearer are inserted when the sock is donned, and a closed toe end, said receptacle including a toe section that is at least in part tapered toward the toe end and projects from the toe end for receiving the toes of the wearer, a tubular generally straight leg section that is adjacent the leg end and is dimensioned to receive at least a portion of the leg of the wearer, and a tubular generally straight foot section extending between the leg section and toe section of the receptacle, said toe, foot and leg sections of the receptacle being knitted of a common high-stretch yarn and being configured to cause the yarn to stretch when the sock is donned, said yarn comprising multiple corespun strands, each of which includes an elastomeric core and an outer sheath of substantially nonelastic fibers, said multiple corespun strands comprising two appositely twisted strands.

* * * * *

(12) EX PARTE REEXAMINATION CERTIFICATE (9782nd)
United States Patent
Svoboda et al.

(10) Number: US 6,158,253 C1
(45) Certificate Issued: Aug. 1, 2013

(54) SEAMLESS, FORM FITTING FOOT SOCK

(75) Inventors: Frank Svoboda, Kansas City, MO (US); H. Darrel Darby, Kansas City, MO (US); Jeffrey C. Dalbey, Leawood, KS (US)

(73) Assignee: U.S. Bank National Association, Saint Louis, MO (US)

Reexamination Request:
No. 90/012,667, Sep. 15, 2012

Reexamination Certificate for:
Patent No.: 6,158,253
Issued: Dec. 12, 2000
Appl. No.: 09/397,421
Filed: Sep. 17, 1999

(51) Int. Cl.
*A41B 11/00* (2006.01)
*D04B 1/22* (2006.01)
*D04B 1/26* (2006.01)

(52) U.S. Cl.
USPC ............................................. 66/178 R; 2/239

(58) Field of Classification Search
None
See application file for complete search history.

(56) References Cited

To view the complete listing of prior art documents cited during the proceeding for Reexamination Control Number 90/012,667, please refer to the USPTO's public Patent Application Information Retrieval (PAIR) system under the Display References tab.

*Primary Examiner* — Patricia Engle (57) ABSTRACT

The highly stretchable, seamless sock conforms to the underlying portion of the body when donned so that there are no undesirable wrinkles or thicknesses in fabric (e.g., ribs, seams, etc) which might cause focal pressure on the foot or leg. The sock comprises a receptacle having an open upper end an opposite, closed toe end. The receptacle includes a toe section that projects from the toe end and is configured to receive the toes of the wearer, a leg section that is adjacent the leg end and is dimensioned to receive at least a portion of the leg of the wearer, a foot section extending between the leg section and toe section of the receptacle, and a heel section extending partly around the circumference of the receptacle between the foot and leg sections. These sections of the receptacle are knitted of a common high-stretch corespun yarn and are configured to cause the yarn to stretch when the sock is donned. Further, the leg section includes an upper portion that is formed of a distinct knitting pattern, such that the compression exerted by the upper portion is different than that exerted by the other sections of the receptacle. The level of compression exerted by the sock may be varied by changing the knitting pattern used to fabricate the sock or by using a different high-stretch core-spun yarn.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 14-16 and 19-21 is confirmed.

Claims 1-4 and 18 are cancelled.

New claims 39-49 are added and determined to be patentable.

Claims 5-13, 17 and 22-38 were not reexamined.

*39. A foot sock as claimed in claim 14,*
*said elastomeric core comprising a spandex filament.*
*40. A foot sock as claimed in claim 14,*
*said leg section including an upper portion adjacent the top end of the receptacle and a lower portion that extends between the upper portion and the foot section,*
*said upper portion of the leg section being formed of a distinct knitting pattern that is different from that of the lower portion of the leg section.*
*41. A foot sock as claimed in claim 40,*
*said distinct knitting pattern comprising a plurality of interlacing looped knit-and-tuck courses.*
*42. A foot sock as claimed in claim 15,*
*said elastomeric core comprising a spandex filament.*
*43. A foot sock as claimed in claim 15,*
*said leg section including an upper portion adjacent the top end of the receptacle and a lower portion that extends between the upper portion and the foot section,*
*said upper portion of the leg section being formed of a distinct knitting pattern that is different from that of the lower portion of the leg section.*
*44. A foot sock as claimed in claim 43,*
*said distinct knitting pattern comprising a plurality of interlacing looped knit-and-tuck courses.*
*45. A foot sock as claimed in claim 16,*
*said elastomeric core comprising a spandex filament.*
*46. A foot sock as claimed in claim 16,*
*said leg section including an upper portion adjacent the top end of the receptacle and a lower portion that extends between the upper portion and the foot section,*
*said upper portion of the leg section being formed of a distinct knitting pattern that is different from that of the lower portion of the leg section.*
*47. A foot sock as claimed in claim 46,*
*said distinct knitting pattern comprising a plurality of interlacing looped knit-and-tuck courses.*
*48. A foot sock as claimed in claim 19,*
*said leg section including an upper portion adjacent the top end of the receptacle and a lower portion that extends between the upper portion and the foot section,*
*said upper portion of the leg section being formed of a distinct knitting pattern that is different from that of the lower portion of the leg section.*
*49. A foot sock as claimed in claim 48,*
*said distinct knitting pattern comprising a plurality of interlacing looped knit-and-tuck courses.*

* * * * *